(12) United States Patent
Montoya et al.

(10) Patent No.: US 11,033,471 B2
(45) Date of Patent: Jun. 15, 2021

(54) PIGMENT COMPOSITIONS

(71) Applicant: L'OREAL, Paris (FR)

(72) Inventors: Mariana Montoya, Berkeley Heights, NJ (US); Angelike A. Galdi, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/848,538

(22) Filed: Dec. 20, 2017

(65) Prior Publication Data
US 2019/0183751 A1    Jun. 20, 2019

(51) Int. Cl.
| | | |
|---|---|---|
| *A61K 8/02* | (2006.01) | |
| *A61K 8/06* | (2006.01) | |
| *A61K 8/19* | (2006.01) | |
| *A61K 8/25* | (2006.01) | |
| *A61K 8/29* | (2006.01) | |
| *C09C 1/00* | (2006.01) | |
| *A61Q 1/02* | (2006.01) | |

(52) U.S. Cl.
CPC ............. *A61K 8/25* (2013.01); *A61K 8/0241* (2013.01); *A61K 8/062* (2013.01); *A61K 8/19* (2013.01); *A61K 8/29* (2013.01); *A61Q 1/02* (2013.01); *C09C 1/0018* (2013.01); *C09C 1/0024* (2013.01); *C09C 1/0051* (2013.01); *A61K 2800/412* (2013.01); *A61K 2800/436* (2013.01); *A61K 2800/5922* (2013.01); *A61K 2800/61* (2013.01); *C01P 2004/61* (2013.01); *C01P 2004/84* (2013.01); *C09C 2200/102* (2013.01); *C09C 2200/308* (2013.01)

(58) Field of Classification Search
CPC ........ A61K 8/25; A61K 8/0241; A61K 8/062; A61K 8/19; A61K 8/29; A61K 2800/412; A61K 2800/436; A61K 2800/5922; A61K 2800/61; A61Q 1/02; C09C 1/0018; C09C 1/0024; C09C 1/0051; C09C 2200/102; C09C 2200/308; C01P 2004/61; C01P 2004/84
See application file for complete search history.

(56) References Cited

U.S. PATENT DOCUMENTS

| | | | |
|---|---|---|---|
| 4,804,533 A | * | 2/1989 | Imamura |
| 6,117,435 A | * | 9/2000 | Painter |
| 6,372,202 B1 | | 4/2002 | Simon |
| 6,663,852 B2 | | 12/2003 | Simon |
| 7,628,998 B2 | | 12/2009 | Shah et al. |
| 8,221,536 B2 | | 7/2012 | Hollman et al. |
| 8,252,298 B2 | | 8/2012 | Maderazzo et al. |
| 2005/0142084 A1 | * | 6/2005 | Ganguly |
| 2007/0207101 A1 | * | 9/2007 | Butts |

FOREIGN PATENT DOCUMENTS

| | | | |
|---|---|---|---|
| FR | 2968945 A1 | | 6/2012 |
| WO | 2012/139244 A1 | * | 10/2012 |
| WO | 2015093614 A1 | | 6/2015 |
| WO | 2017072129 A1 | | 5/2017 |

* cited by examiner

*Primary Examiner* — Alma Pipic
(74) *Attorney, Agent, or Firm* — Laetitia Leproust; Runzhi Zhao

(57) ABSTRACT

The instant disclosure relates to a composition for topical application to the skin comprising a first pearlescent uncoated pigment having an average particle size of 25 um or less; a second pearlescent pigment having an average particle size of 25 um or less, completely or partially coated with one or more layers of metal oxides; a first mica having an average size of 42 um or less, completely or partially coated with one or more layers of red iron oxide; and a second mica having an average size of 25 um or less, completely or partially coated with one or more layers of titanium dioxide. It also relates to methods of using said compositions.

13 Claims, No Drawings

PIGMENT COMPOSITIONS

FIELD OF THE DISCLOSURE

The instant disclosure relates to cosmetic compositions intended for application to the skin, in particular intended for skin care, capable of giving the skin a healthy-looking appearance, while at the same time retaining its natural appearance.

BACKGROUND

It is generally accepted that beautiful skin has a transparent quality with uniform undertones of color. The basis for this attractive, natural-looking appearance is skin structure. This appearance is influenced by a number of factors.

The outer layer of human skin is a semi-transparent layer known as the stratum corneum. Underlying the stratum corneum is a layer of skin that has the blood vessels and pigments of the body. The reddish hue of the blood vessels, hemoglobin, and the brown/black hue of melanin combine to produce, through the transparency of the stratum corneum, the skin's color. Color cosmetic manufacturers know that matching the skin tone/color is important to provide a desirable cosmetic product, especially foundation make-up compositions. A foundation cosmetic or makeup composition is often used to provide a uniform "base" of skin color onto which is applied other colored cosmetics, such as a blush. A user prefers a foundation cosmetic that not only matches his/her skin color but that also gives his/her skin an even, natural or healthy glow.

Consequently, there remains a need for a cosmetic composition which makes it possible to return to a complexion, that offers a more radiant, more uniform appearance, in summary to provide a universal glow and healthy-looking appearance.

SUMMARY OF THE DISCLOSURE

The instant disclosure relates to compositions for topical application and methods of using the compositions to provide a universal glow and healthy-looking appearance. The compositions improve the appearance of skin and provide a more radiant, more uniform appearance.

The compositions of the instant disclosure typically include:
  a. a first pearlescent uncoated pigment having an average particle size of 25 um or less;
  b. a second pearlescent pigment having an average particle size of 25 um or less, completely or partially coated with one or more layers of metal oxides;
  c. a first mica having an average size of 42 um or less, completely or partially coated with one or more layers of red iron oxide;
  d. a second mica having an average size of 25 um or less, completely or partially coated with one or more layers of titanium dioxide.

In one or more embodiments, the first pearlescent pigment is synthetic fluorphlogopite.

In some embodiments, the second pearlescent pigment is completely or partially coated with one or more layers of metal oxides chosen from the group consisting of titanium dioxide, tin dioxide, iron dioxide, aluminum dioxide, and mixtures thereof.

In one or more embodiments, the average size of the particles of the first pearlescent pigment is from about 1 to about 15 um.

In some embodiments, the second pearlescent pigment is completely or partially coated with titanium dioxide and tin dioxide.

In one or more embodiment, the average size of the particles of the second pearlescent pigment is from about 5 to about 25 um.

In some embodiments, the first mica is further completely coated or partially coated with one or more layers of titanium dioxide, tin dioxide, alumina, or mixture thereof.

In one embodiment, the first mica is further completely coated or partially coated with titanium dioxide.

In some embodiments, the second mica is further completely coated or partially coated with one or more layers of titanium dioxide, tin dioxide, alumina, or mixture thereof.

In one embodiment, the second mica is further completely coated or partially coated with yellow iron oxide.

In some embodiments, the total amount of the first pearlescent pigment in the composition is present in a ratio of about 0.05 to about 0.6, based on the total weight of the composition.

In one or more embodiments, the total amount of the second pearlescent pigment in the composition is present in a ratio of about 0.05 to about 0.6, based on the total weight of the composition.

In one embodiment, the total amount of the first mica in the composition is present in a ratio of about 0.05 to about 0.6, based on the total weight of the composition.

In various embodiments, the total amount of the second mica in the composition is present in a ratio of about 0.05 to about 0.6, based on the total weight of the composition.

In some embodiments, the compositions further include boron nitride.

In one or more embodiments, the total amount of the boron nitride in the composition is from about 0.1% to about 7%, based on the total weight of the composition.

In some embodiments, the compositions are in a form of an emulsion, a powder, a cream-to-powder cosmetic, a gel, a pomade, a solution, a stick, a suspension, or a wet/dry foundation.

In one embodiment, the composition is in a form of oil-in-water emulsion.

In some embodiments, the compositions further comprise one or more skin active ingredients.

In various embodiments, the one or more skin active ingredients are selected from the group consisting of a humectant, a moisturizing ingredient, an anti-aging agent, a depigmenting agent, an anti-wrinkle agent, an agent that treats oily skin, and a mixture thereof.

In one or more embodiments, the one or more skin active ingredients are selected from the group consisting of adenosine, ascorbic acid, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, a coenzyme, and a mixture thereof.

The instant disclosure also relates to methods for applying the composition to the skin in order to provide a universal glow and healthy-looking appearance.

Another aspect of the instant disclosure can include the following:
  a. a first synthetic fluorphlogopite having an average particle size of 25 uM.
  b. a first mica having an average size of 42 uM or less, completely or partially coated with one or more layers of red iron oxides, further coated with titanium dioxide;

c. a second mica having an average size of 42 uM or less, completely or partially coated with one or more layers of titanium dioxide, further coated with iron dioxide.

In one or more embodiments, the first synthetic fluorphlogopite is uncoated.

In various embodiments, the compositions further comprise a second synthetic fluorphlogopite having an average particle size of 25 um or less, completely or partially coated with one or more layers of metal oxides.

In some embodiments, the second synthetic fluorphlogopite is completely or partially coated with one or more layers of metal oxides chosen from the group consisting of titanium dioxide, tin dioxide, iron dioxide, aluminum dioxide, and mixtures thereof.

In one embodiment, the second synthetic fluorphlogopite is completely or partially coated with titanium dioxide and tin dioxide.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE DISCLOSURE

The instant disclosure relates to compositions for topical application and methods of using the compositions to provide a universal glow and healthy-looking appearance. The compositions improve the appearance of skin and provide a more radiant, more uniform appearance.

The compositions of the instant disclosure, in the broadest sense, typically include a first pearlescent uncoated pigment having an average particle size of 25 um or less; a second pearlescent pigment having an average particle size of 25 um or less, completely or partially coated with one or more layers of metal oxides; a first mica having an average size of 42 um or less, completely or partially coated with one or more layers of red iron oxide; a second mica having an average size of 25 um or less, completely or partially coated with one or more layers of titanium dioxide.

Upon application to the skin, the compositions provide a universal glow and healthy-looking appearance whatever skin type and ethnicities.

Even though the uses of pearlescent pigments and mica coated completely or partially with one or more layers of metal oxides are well known in make-up products, the uniqueness of the present disclosure is the balance of white to colored pigments and powders as well as the pink to bronze pearl balance. The ratio of the different pearlescent pigments and mica composition give the blend some specific characteristics. One of the unique aspect in the present disclosure is the requirement for having small particles size of each of the powders and pearls. The average particle size of the pearls and pigments is the smallest when compared to the competitor products after a microscope analysis on the glow moisturizers. Another unique characteristic of the blend presented in the present disclosure is the transparency and the little effect on skin tones. The pearls and pigments have relatively small particle size t which prevent the optical effect from looking glittery and artificial. The blend was carefully created to incorporate the correct balances of pinks, bronzes, and whites to create a color that will not affect the overall tone of fair to deep skin while providing a noticeable and instant glow. The unique ratios between the blend components result to a formula tone which is both appealing in bulk and flattering on Caucasian, Asian, Hispanic, African American and Indian skin tones (i.e. a "universal glow").

Pearlescent Pigment

Pearlescent pigments are examples of mica composition pigments. The term "pearlescent pigment" means colored particles of any form, which may optionally be iridescent, as produced in the shells of certain mollusks, or which are synthesized, and which exhibit a "pearlescent" coloring effect by optical interference.

In some embodiments, the at least first pearlescent uncoated pigment of (a) can be, for example, uncoated or coated. By way of non-limiting example, pearlescent pigments may be chosen from synthetic fluorphlogopite based, multilayered pigments in order to provide a pearlescent effect. In at least certain embodiments, the at least one pearlescent pigment may be chosen from synthetic fluorphlogopite pigments that are completely or partially coated with one or more layers of metal oxides, such as but not limited to titanium dioxide, tin oxide, iron oxide, aluminum dioxide, or mixtures thereof. The color of the pearlescent pigments used in the instant disclosure is of a white color that will balance the other colors present in the overall inventive composition.

The first pearlescent uncoated pigment may be present and have an average particle size from about 25 um, 24 um, 23 um, 22 um, 21 um, 20 um, 19 um, 18 um, 17 um, 16 um, 15 um to about 15 um, 14 um, 13 um, 12 um, 11 um, 10 um, 9 um, 8 um, 7 um, 6 um, 5 um, 4 um, 3 um, 2 um, 1 um or less. The average particle size may be measured as a volume average particle size, with a laser granulometer, for instance the Mastersizer 2000® machine from Malvern and/or the BI90+® machine from Brookhaven Instrument Corporation. In some embodiment, the first pearlescent uncoated pigment is synthetic fluorphlogopite.

In some embodiments, the total amount of the first pearlescent pigment in the composition is present in a ratio of about 0.05, 0.06, 0.07, 0.08, 0.09, 0.1, 0.2, 0.3 to about 0.3, 0.4, 0.45, 0.5, 0.55, or 0.6, based on the total weight of the composition.

In some embodiments, the second pearlescent pigment may be present and may be completely or partially coated with one or more layers of metal oxides chosen from the group consisting of titanium dioxide, tin dioxide, iron dioxide, aluminum dioxide, and mixtures thereof.

The second pearlescent pigment may be present and have an average particle size from about 25 um, 24 um, 23 um, 22 um, 21 um, 20 um, 19 um, 18 um, 17 um, 16 um, 15 um to about 15 um, 14 um, 13 um, 12 um, 11 um, 10 um, 9 um, 8 um, 7 um, 6 um, 5 um, 4 um, 3 um, 2 um, 1 um or less.

In some embodiments, the second pearlescent pigment is composed of 68% of synthetic fluorphlogopite, 31% of titanium dioxide (CI77891), and 1% of tin oxide.

According to one embodiment, the composition comprises synthetic fluophlogopite particles coated with a mixture of titanium dioxide and tin oxide, are sold under the brand Syncrystal Silk Silver by the company Eckart.

In some embodiments, the total amount of the second pearlescent pigment in the composition is present in a ratio of about 0.05, 0.06, 0.07, 0.08, 0.09, 0.1, 0.2, 0.3 to about 0.3, 0.4, 0.45, 0.5, 0.55, or 0.6, based on the total weight of the composition.

The color of the pigments in themselves can advantageously be evaluated by colorimetric measurements of the lightness ($L^*$) and of the saturation ($c^*$) in the CIE Lab 1976 colorimetric space, and can for example be carried out using a Minolta colorimetric Chromameter CR400®.

Mica

In addition to the components described above, the compositions can additionally include mica. As used herein, the expression "mica composition" means a pigment comprising at least one type core composed of mica, and at least one coat containing including at least titanium dioxide and iron oxide.

As examples of mica, mention may be made of pigments such as mica titanium dioxide coated with iron oxide, mica titanium dioxide coated with chromium oxide, mica titanium dioxide coated with an organic colorant, in particular of the type mentioned above, and nacre pigments based on bismuth oxychloride. They may also be particles of mica on the surface of which at least two successive layers of metal oxides and/or organic coloring substances have been superimposed.

The mica of (c) may be present and completely or partially coated with one or more layers of red iron oxide. These micas may further be completely coated or partially coated with one or more layers of titanium dioxide, tin dioxide, alumina, or mixture thereof. In some embodiments, the first mica is further completely coated or partially coated with titanium dioxide. In the present disclosure, the color achieved with the red iron oxides layers makes the mica composition having a pink color.

The mica may be present and have an average particle size from about 42 um, 41 um, 40 um, 39 um, 38 um, 36 um, 34 um, 32 um, 30 um, 28 um, 26 um, 24 um, 22 um, 20 um to about 20 um, 18 um, 16 um, 15 um, 14 um, 13 um, 12 um, 11 um, 10 um, 9 um, 8 um, 7 um, 6 um, 5 um, 4 um, 3 um, 2 um, 1 um or less.

In some embodiments, the first mica is composed of 61.5% of mica, 24% of iron oxide (CI77491), and 14.5% of titanium dioxide (CI77891).

According to one embodiment, the composition comprises mica particles coated with a mixture of iron oxide and titanium dioxide, are sold under the brand Gemtone Tan Opal G 005 by the company Basf Personal Care Ingredients.

In other embodiments, the total amount of the first mica in the composition is present in a ratio of about 0.05, 0.06, 0.07, 0.08, 0.09, 0.1, 0.2, 0.3 to about 0.3, 0.4, 0.45, 0.5, 0.55, or 0.6, based on the total weight of the composition.

The mica of (d) may be present and completely or partially coated with one or more layers of titanium dioxide. These micas may further be completely coated or partially coated with one or more layers of titanium dioxide, tin dioxide, alumina, or mixture thereof. In some embodiments, the second mica is further completely coated or partially coated with yellow iron oxide. In the present disclosure, the color achieved with the yellow iron oxides layers makes the mica composition having a bronze color.

The mica of (d) may be present and have an average particle size from about 25 um, 24 um, 23 um, 22 um, 21 um, 20 um, 19 um, 18 um, 17 um, 16 um, 15 um to about 15 um, 14 um, 13 um, 12 um, 11 um, 10 um, 9 um, 8 um, 7 um, 6 um, 5 um, 4 um, 3 um, 2 um, 1 um or less.

In some embodiments, the second mica is composed of 49% of mica, 32% of titanium dioxide (CI77891), and 19% of iron oxide (CI77491).

According to one embodiment, the composition comprises mica particles coated with a mixture of titanium dioxide and iron oxide, are sold under the brand Colorona Oriental Beige by the company Merck.

In other embodiments, the total amount of the second mica in the composition is present in a ratio of about 0.05, 0.06, 0.07, 0.08, 0.09, 0.1, 0.2, 0.3 to about 0.3, 0.4, 0.45, 0.5, 0.55, or 0.6, based on the total weight of the composition.

Filler

The topical compositions can also include one or more fillers. For example, the filler can be boron nitride. The fillers may be of mineral or organic origin, natural or synthetic in nature in order to provide oil absorption or optical effects. Oil absorption fillers may impart a matte effect and non-greasy feeling onto the skin. Optical effects fillers may impart a soft-focus/haze/blur effect to the skin, provide the skin with a more uniform appearance, reduce the appearance of skin imperfections or discoloration, or reduce the visibility of pores.

Mention may be made as examples of oil-absorbing fillers: *Zea may* (corn) starch, magnesium oxide, nylon-12, nylon-66, cellulose, polyethylene, talc, talc (and) methicone, talc (and) dimethicone, perlite, sodium silicate, pumice, ptfe, polymethyl methacrylate, *Oryza sativa* (rice) starch, aluminum starch octenylsuccinate, potato starch modified, alumina, calcium sodium borosilicate, magnesium carbonate, hydrated silica, dimethicone/vinyl dimethicone crosspolymer, sodium carboxylmethyl starch. According to one embodiment, the oil-absorbing filler comprises spherical microparticles of porous silica having a mean particle size from 0.5 to m whose INCI name is silica sold by the company JCG Catalysts and Chemicals under the name Spheron L-1500. According to another embodiment, the oil absorbing filler comprises hydrophobic aerogel particles whose INCI name is silica silylate sold by Dow Corning under the name VM-2270 Aerogel Fine Particles.

Mention may be made as examples of optical effects fillers: bismuth oxychloride, silica silylate, boron nitride, iron oxide, calcium carbonate, calcium sulfate (and) iron oxides, sodium potassium aluminum silicate.

Mention may be made as examples of fillers which provide both oil-absorbing and optical effects: silica, silica (and) methicone, silica (and) dimethicone, polysilicone-22, polysilicone-8, polysilicone-11, methyl metacrylate crosspolymer, polymethylsilsesquioxane, methylsilanol/silicate crosspolymer, vinyl dimethicone/methicone silsesquioxane crosspolymer, diphenyl dimethicone/vinyl diphenyl dimethicone silsesquioxane crosspolymer, and styrene/acrylates copolymer.

The filler may be present in the composition according to the disclosure, at a concentration, from about 0.1% to 15%, in some embodiments from about 0.1% to 10%, and in some embodiments from about 0.5% to 9% based on the total weight of the composition. Thus, in various embodiments, the fillers may be present in an amount from about 0.1%, 0.2%, 0.3%, 0.4%, 0.5%, 1%, 2%, 3%, 4% to about 4%, 5%, 5.5%, 6%, 6.5% or 7%, based on the total weight of the composition.

Oils/Fatty Compounds

The cosmetic composition comprises one or more oils, for example, silicone oils, fluoro oils, hydrocarbon-based oils, etc. The term "oil" means any fatty substance which is in liquid form at room temperature (20-25° C.) and at atmospheric pressure (760 mmHg). Often, at least one of the oils in the cosmetic composition is part of an oily phase. An "oily phase" is a phase comprising at least one oil that may include additional liposoluble and lipophilic ingredients and the fatty substances. Oil that is suitable for use herein may be volatile or non-volatile. The term "volatile oil" relates to an oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to oil which remains on the skin or the keratin fiber, at room temperature and atmospheric pressure, for at least several hours and which in particular has a vapor pressure of less than $10^{-3}$ mmHg (0.13 Pa).

Silicone Oils

The term "silicone oil" relates to oil comprising at least one silicon atom, and especially at least one Si—O group. A non-limiting example of a silicone oil derivative is pentaerythrityl tetraethylhexanoate, (for example Trivent PE, available form Alzo).

The cosmetic compositions described herein may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl) trimethylsiloxysilicates.

Other examples of silicone oils that may be mentioned include volatile linear or cyclic silicone oils, especially those with a viscosity 8 centistokes ($8\times10^6$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The term "fluoro oil" relates to oil comprising at least one fluorine atom. The cosmetic compositions described herein may comprise one or more fluoro oils. For example, the onee or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. The cosmetic compositions described herein may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

(i) hydrocarbon-based oils of plant origin, such as butyrospermum parkii (shea) butter, or such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, *quinoa* oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 40 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ≥10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *Eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C $C_8$-$C_{16}$ esters, and isohexyl neopentanoate.

As mentioned previously, one or more oils of the cosmetic composition is often part of an oily phase. The oily phase may include other fatty substances, mixed with or dissolved in the oil. A fatty substance that may be present in the oily phase may be, for example:

(i) a fatty acid chosen from fatty acids comprising from 8 to 30 carbon atoms, such as stearic acid, lauric acid, palmitic acid and oleic acid;

(ii) a wax chosen from waxes such as lanolin, beeswax, carnauba or candelilla wax, paraffin waxes, lignite waxes, microcrystalline waxes, ceresin or ozokerite, or synthetic waxes, such as polyethylene waxes or Fischer-Tropsch waxes;

(iii) a gum;

(iv) a pasty compound, such as polymeric or non-polymeric silicone compounds, esters of a glycerol oligomer, arachidyl propionate, fatty acid triglycerides and derivatives thereof.

The overall oily phase may represent 5 wt. % to 95 wt. %, 10 wt. % to 80 wt. %, 20 wt. % to 70 wt. %, or 30 wt. % to 60 wt. % of the cosmetic composition. The overall aqueous phase may represent 5 wt. % to 95 wt. %, 20 wt. % to 90 wt. %, 30 wt. % to 80 wt. %, or 40 wt. % to 70 wt. % of the cosmetic composition.

Thickeners

The cosmetic compositions described herein may include one or more thickeners. The thickeners may be in an amount of 0.1 wt. % to 20 wt. %, 0.1 to 10 wt. %, 0.1 wt. % to 9 wt. %, 0.2 wt. % to 9 wt. %, 0.3 wt. % to 9 wt. %, 0.4 wt. % to 8 wt. %, 0.5 wt. % to 5 wt. %, 1 wt. % to 5 wt. %, or 2 wt. % to 4 wt. %. Further, the amount of thickener may be from 0.1, 0.2, 0.3, 0.4, 0.5, 0.6, 0.7, 0.8, 0.9, 1.0, or 1.5 wt. % to 2, 3, 4, 5, 6, 7, 8, 9, 10, 15, or 20 wt. %.

The one or more thickeners may be xanthan gum, guar gum, biosaccharide gum, cellulose, acacia Seneca gum, *sclerotium* gum, agarose, pechtin, gellan gum, hyaluronic acid. Additionally, the one or more thickeners may include polymeric thickeners selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the composition includes ammonium polyacryloyldimethyl taurate and/or sodium polyacrylate.

Many thickeners are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 U.S. Pat. No. 4,599,379 and EP 228,868, which are all incorporated herein by reference in their entirety.

c. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

d. Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS 11 from Michel Mercier Products Inc.

e. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived form callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Organic Solvent

In accordance with the disclosure, one or more organic solvent is present in the composition. The organic solvent present in the cosmetic composition, according to the disclosure, includes, but is not limited to, alcohol denature, butylene glycol, C12-15 alkyl benzoate, glycerin, propylene, glycol, caprylyl glycol, or combinations thereof. Although these solvents are given as an example, it will be appreciated that other solvents compatible with cosmetic applications known in the art may be used.

In accordance with the various embodiments, organic solvent may be present in a given composition in an amount of from about 0.1% to about 30%, alternatively from about 0.2% to about 28%, alternatively from about 0.3% to about 25%, or any suitable combination, sub-combination, range, or sub-range thereof by weight, based on the weight of the composition. One of ordinary skill in the art, however, will appreciate that other ranges are within the scope of the invention Water In accordance with the various embodiments, water may be present in a given composition in an amount of from about 25% to about 80%, alternatively from about 40% to about 75%, alternatively from about 45% to about 70%, alternatively from about 55% to about 65% or any suitable combination, sub-combination, range, or sub-range thereof by weight, based on the weight of the composition. One of ordinary skill in the art, however, will appreciate that other ranges are within the scope of the invention.

Optional Components

In some embodiments, there may be one or more actives present in the cosmetic composition, according to the disclosure, the actives selected from, for example, humectant, antimicrobial, antioxidant, preservative, vitamin, vitamin derivative, UV filter, vegetable extract; and dye/pigment, filler, thickener, polymer, penetrant, fragrance, dispersant, film-forming agent; ceramide; opacifier and combinations thereof.

In some embodiments, there may be one or more actives present in the cosmetic composition, according to the disclosure, the actives selected from, for example, adenosine, ascorbic acid, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, a coenzyme, and a mixture thereof.

In some embodiments, there may be one or more other components present in the cosmetic composition, according to the disclosure, the other components selected from sodium hydroxide, disodium EDTA, sodium citrate, sodium hyaluronate, capryloyl salicylic acid, lactic acid, methyl dihydro jasmonate, acetyl trifluoromethyl phenyl valyglycine, pentaerythrityl tetra-di-t-butyl hydroxydrocinnamate, n-hydroxysuccinimide, palmitoyl oligopeptide, chrysin, palmitoyl tetrapeptide-7, yeast extract, citric acid and combinations thereof.

In accordance with the various embodiments, the amount of actives and other components present in the composition may be from about 0% to about 50%, alternatively from about 0.5% to about 30%, alternatively from about 1.5% to about 20%, alternatively from about 5% to about 15%, or any suitable combination, sub-combination, range, or sub-range thereof by weight, based on the weight of the composition.

In some embodiments, one or more actives, alone or in combination, may be present in the composition according to the disclosure from about 0.05% to about 50% by weight, alternatively from about 0.05% to about 2.5% by weight, alternatively from about 0.1% to about 2%, alternatively from about 0.25% to about 1.5%, alternatively from about 0.5% to about 1.25%, or any suitable combination, sub-combination, range, or sub-range thereof by weight, based on the weight of the composition.

In some embodiments, one or more other components, such as preservatives, vitamins, and the like, alone or in combination, may be present in the composition according to the disclosure from about 0.05% to about 50% by weight, alternatively from about 0.05% to about 25% by weight, alternatively from about 0.1% to about 10%, alternatively from about 0.25% to about 5%, alternatively from about 0.5% to about 3.5%, or any suitable combination, sub-combination, range, or sub-range thereof by weight, based on the weight of the composition. In some exemplary embodiments, preservatives may include sodium salicylate, and vitamins may include ascorbic acid, tocopherol and combinations thereof.

Preservatives

The compositions according to the disclosure may include one or more preservatives. In a desirable embodiment, the preservatives may include organic acids, parabens, formaldehyde donors, phenol derivatives, quaternary ammoniums, alcohols, isothiazolones, and combinations thereof.

Examples of alcohol preservative systems include, but are not limited to, ethanol, benzyl alcohol, dichlorobenzyl alcohol, phenoxyethanol, and combinations thereof.

Examples of isothiazolone preservative include, but are not limited to, methylchloroisothiazolinone, methylisothiazolinone, and combinations thereof. Other suitable preservatives include, but are not limited to, chloracetamide, triclosan and iodopropynyl butylcarbamate, pyridine derivatives (e.g., pyrithione and zinc pyrithione), chlorphenesin, phenyl mercuric salts, phenoxyethanol, and other known preservative.

Preservatives may be present in the composition according to the invention, at a concentration, from about 0.01% to 25%, in some embodiments from about 0.1% to 20%, and in some embodiments from about 0.5% to 15% by weight, all weights based on the total weight of the composition. Thus, in various embodiments, a preservative may be present in a composition in a weight percent amount from 0.01, 0.02, 0.03, 0.04, 0.05, 0.06, 0.07, 0.08, 0.09, 0.5, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0 to 25.0 percent by weight, including increments and ranges there between.

Emulsifiers

Emulsifiers are well known in the art and include amphoteric, anionic, cationic or nonionic emulsifiers, used alone or as a mixture, and optionally with a co-emulsifier.

A composition according to the present disclosure may contain emulsifier and co-emulsifying surfactants present in particular in a proportion ranging from 0.1% to 30% by weight and in particular ranging from 0.5% to 15% by weight relative to the total weight of the composition.

These surfactants may be chosen from amomc and nomomc surfactants. Reference may be made to Kirk-Othmer's Encyclopedia of Chemical Technology, Volume 22, pp. 333-432, 3rd Edition, 1979, Wiley, for the definition of the properties and functions (emulsifying) of surfactants, in particular pp. 347-377 of this reference, for the anionic and nonionic surfactants.

Sunscreen Actives

Suitable UV-screening agents include, but are not limited to, cinnamic derivatives; anthranilates; salicylic derivatives; dibenzoylmnethane derivatives; camphor derivatives; benzophenone derivatives; β,β-diphenylacrylate derivatives; triazine derivatives; benzotriazole derivatives; benzalmalonate derivatives, especially those cited in U.S. Pat. No. 5,624,663; benzimidazole derivatives; imidazolines; bis-benzoazolyl derivatives as described in patents EP669323 and U.S. Pat. No. 2,463,264; p-aminobenzoic acid (PABA) derivatives; methylene bis(hydroxyphenylbenzotriazole) derivatives as described in applications U.S. Pat. Nos. 5,237,071, 5,166,355, GB2303549, DE19726184 and EP893119; benzoxazole derivatives as described in patent applications EP0832642, EP1027883, EP1300137 and DE10162844; screening polymers and screening silicones such as those described especially in patent application WO 93/04665; dimers derived from oa-alkylstyrene such as those described in patent application DE 19855649; 4,4-diarylbutadienes such as those described in patent applications EP0967200, DE19746654, DE19755649, EP-A-1008586, EPI 133980 and EP1133981, merocyanine derivatives such as those described in patent applications WO 04/006878, WO 05/058269 and WO 06/032741; and mixtures thereof.

As examples of complementary organic photoprotective agents, mention may be made of those denoted herein below under their INCI name:

Cinnamic Derivatives:
  Ethylhexyl Methoxycinnamate sold in particular under the trade name "Parsol® MCX" by DSM Nutritional Products, Isopropyl Methoxycinnamate, Isoamyl Methoxycinnamate sold under the trade name "Neo Heliopan® E 1000" by Symrrise, DEA Methoxycinnamate, Diisopropyl Methyklcinnamate, Glyceryl Ethylhexanoate Dimethoxycinnamate.

Dibenzoylmethane Derivatives:
  Butyl Methoxydibenzoylmethane sold especially under the trade name "Parsol® 1789" by DSM, Isopropyl Dibenzoylmethane.

Para-Aminobenzoic Acid Derivatives:
  PABA, Ethyl PABA, Ethyl Dihydroxypropyl PABA, Ethylhexyl dimethyl PABA sold in particular under the name "Escalol™ 507" by ISP, Glyceryl PABA, PEG-25 PABA sold under the name "Uvinul® P25" by BASF.

Salicylic Derivatives:
  Homosalate sold under the name "Eusolex® H-IMS" by Rona/EM Industries, Ethylhexyl Salicylate sold under the name "Neo Heliopan® OS" by Symrise, Dipropylene Glycol Salicylate sold under the name "Dipsal™" by Scher, TEA Salicylate sold under the name "Neo Heliopan® TS" by Symrise.

β,β-Diphenlacrylate Derivatives:
  Octocrylene sold in particular under the trade name "Uvinul® N539" by BASF, Etocrylene sold in particular under the trade name "Uvinul N35" by BASF.

Benzophenone Derivatives:
  Benzophenone-1 sold under the trade name "Uvinul® 400" by BASF, Benzophenone-2 sold under the trade name "Uvinul® D50" by BASF, Benzophenone-3 or Oxybenzone sold under the trade name "Uvinul® M40" by BASF, Benzophenone-4 sold under the trade name "Uvinul® MS40" by BASF, Benzophenone-5, Benzophenone-6 sold under the trade name "Helisorb® 11" by Norquay, Benzophenone-8 sold under the trade name "Spectra-Sorb UV-24" by American Cyanamid, Benzophenone-9 sold under the trade name "Uvinul® DS-49" by BASF, Benzophenone-12, n-Hexyl 2-(4-diethylamino-2-hydroxybenzoyl)benzoate sold under the trade name "Uvinul® A+" or as a mixture with octyl methoxycinnamate under the trade name "Uvinul® A+B" by BASF.

Benzylidenecamphor Derivatives:
  3-Benzylidene Camphor manufactured under the name "Mexoryl™ SD" by Chimex, 4-Methylbenzylidene Camphor sold under the name "Eusolex® 6300" by Merck, Benzylidene Camphor S ulfonic Acid manufactured under the name "Mexoryl™ SL" by Chimex, Camphor Benzalkonium Methosulfate manufactured under the name "Mexoryl™ SO" by Chimex, Terephthalylidene Dicamphor Sulfonic Acid manufactured under the name "Mexoryl™ SX" by Chimex, Polyacrylamidomethyl Benzylidene Camphor manufactured under the name "Mexoryl™ SW" by Chimex.

Phenylbenzimidazole Derivatives:
  Phenylbenzimidazole Sulfonic Acid sold in particular under the trade name "Eusolex® 232" by Merck, Disodium Phenyl Dibenzimidazole Tetrasulfonate sold under the trade name "Neo Heliopan® AP" by Symrise.

Phenylbenzotriazole Derivatives:
  Drometrizole Trisiloxane sold under the name "Silatrizole" by Rhodia Chimie, Methylene bis-Benzotriazolyl Tetramethylbutyl-phenol sold in solid form under the trade name "MIXXIM BB/100" by Fairmount Chemical, or in micronized form as an aqueous dispersion under the trade name "Tinosorb M" by Ciba Specialty Chemicals.

Triazine Derivatives:
  bis-Ethylhexyloxyphenol Methoxyphenyl Triazine sold under the trade name "Tinosorb® S" by BASF, Ethylhexyl Triazone sold in particular under the trade name "Uvinul® T150" by BASF, Diethylhexyl Butamido Triazone sold under the trade name "Uvasorb® HEB" by Sigma 3V, 2,4,6-tris(dineopentyl 4'-aminobenzahlmalonate)s-triazine, 2,4,6-tris(diisobutyl 4'-aminobenzalmalonate)s-triazine, 2,4-bis(dineopentyl 4'-aminobenzalmalonate)-6-(n-butyl 4'-aminobenzoate)-s-triazine, symmetrical triazine screening agents described in U.S. Pat. No. 6,225,467, patent application WO 2004/085412 (see compounds 6 and 9) or the document "Symmetrical Triazine Derivatives" IP.COM Journal, IP.COM Inc., West Henrietta, N.Y., US (20 Sep. 2004), especially 2,4,6-tris(biphenyl)-1,3,5-triazines (in particular 2,4,6-tris(biphenyl-4-yl)-1,3,5-triazine and 2,4,6-tris(terphenyl)-1,3,5-triazine, which is included in patent applications WO 06/035000, WO 06/034982, WO 06/034991, WO 06/035007, WO 2006/034992 and WO 2006/034985).

Anthranilic Derivatives:
  Menthyl Anthranilate sold under the trade name "Neo Heliopan® MA" by Syrnrise.

Imidazoline Derivatives:
  Ethylhexyl Dimethoxybenzylidene Dioxoimidazoline Propionate.

Benzalmalonate Derivatives:
  Polyorganosiloxane containing benzalmalonate functions, for instance Polysilicone-15, sold under the trade name "Parsol® SLX" by DSM Nutritional Products.

4,4-Diarylbutadiene Derivatives:
  1,1-dicarboxy(2,2'-dimethylpropyl)-4,4-diphenylbutadiene.

Benzoxazole Derivatives:
  2,4-bis[5-(1-dimethylpropyl)benzoxazol-2-yl-(4-phenyl)imino]-6-(2-ethylhexyl)imino-1,3,5-triazine sold under the name Uvasorb® K2A by Sigma 3V, and mixtures thereof.

Prefered Organic Screening Agents are Chosen from:
  Ethylhexyl Methoxycinnamate, Ethylhexyl Salicylate, Homosalate, Butyl Methoxydibenzoylmethane, Octocrylene, Phenylbenzimidazole Sulfonic Acid, Benzophenone-3, Benzophenone-4, Benzophenone-5, n-Hexyl 2-(4-diethylamino-2-hydroxybenzoyl)benzoate, 4-Methylbenzylidene Camphor, Terephthalylidene Dicamphor Sulfonic Acid, Disodium Phenyl Dibenzimidazole Tetrasulfonate, Methylene Bis-Benzotriazolyl Tetramethylbutylphenol, Bis-Ethylhexyloxyphenol Methoxyphenyl Triazine, Ethylhexyl triazone, Diethylhexyl Butamido Triazone, 2,4,6-Tris(dineopentyl 4'-aminobenzalmalonate)-s-triazine, 2,4,6-Tris(diisobutyl 4'-aminobenzalmalonate)-s-triazine, 2,4-Bis(dineopentyl 4'-aminobenzalmalonate)-6-(n-butyl 4'-aminobenzoate)-s-triazine, 2,4,6-Tris(biphenyl-4-yl)-1,3,5-triazine, 2,4,6-Tris(terphenyl)-1,3,5-triazine, Drometrizole Trisiloxane, Polysilicone-15, 1,1-dicarboxy(2,2'-dimethylpropyl)-4,4-diphenylbutadiene, 2,4-bis[5-1 (dimethylpropyl)benzoxazol-2-yl-(4-phenyl)imino]-6-(2-ethylhexyl)imino-1,3,5-triazine, and mixtures thereof.

Other Optional Ingredients

The compositions according to the disclosure may include one more of a variety of optional ingredient, selected from but not limited to, one or more standard cosmetic adjuvants chosen from: oils, waxes, organic solvents, fillers, ionic or nonionic, hydrophilic or lipophilic thickeners, softeners, humectants, opacifiers, stabilizers, emollients, silicones, antifoams, fragrances, preserving agents, surfactants, active agents, coloring agents, cationic polymers, propellants, neutralizing or pH-adjusting agents (e.g., citric acid, triethylamine (TEA) and sodium hydroxide), conditioning or softening agents (e.g., panthenol and allantoinin), extracts, such as botanical extracts, free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in whatever phase or phases is/are present in the cosmetic composition (i.e., aqueous and/or fatty (oil) phase) or any other ingredient usually used in cosmetics and/or dermatology.

Those skilled in the art will take care to select the optional additional compound(s) mentioned above and/or the amounts thereof such that the advantageous properties intrinsically associated with the compositions, in accordance with the invention, are not, or are not substantially, adversely affected by the envisaged addition(s). Those skilled in the art will choose said active agent(s) according to the desired effect on the skin, hair, eyelashes, eyebrows, or nails.

Implementation of the present disclosure is provided by way of the following examples. The examples serve to illustrate the technology without being limiting in nature.

As used herein, the expression "One or more" means at least one and thus includes individual components as well as mixtures/combinations.

The compositions and methods of the present invention can comprise, consist of, or consist essentially of the essential elements and limitations of the invention described herein, as well as any additional or optional ingredients, components, or limitations described herein or otherwise useful.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about".

All percentages, parts and ratios herein are based upon the total weight of the compositions of the present invention, unless otherwise indicated.

As used herein, all ranges provided are meant to include every specific range within, and combination of subranges between, the given ranges. Thus, a range from 1-5, includes specifically 1, 2, 3, 4 and 5, as well as subranges such as 2-5, 3-5, 2-3, 2-4, 1-4, etc.

As used herein, a range of ratios is meant to include every specific ratio within, and combination of subranges between, the given ranges.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The foregoing description illustrates and describes the disclosure. Additionally, the disclosure shows and describes only the exemplary embodiments but, as mentioned above, it is to be understood that it is capable to use in various other combinations, modifications, and environments and is capable of changes or modifications within the scope of the disclosed concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

EXAMPLES

Inventive Composition

The inventive composition is represented in Table 1 below.

TABLE 1

| | Inventive Formula | |
|---|---|---|
| Pearl Pigments and Mica | Ingredients | Inventive formula |
| | pH ADJUSTER | 0.015 |
| | DISODIUM EDTA | 0.1 |
| | CAPRYLOYL SALICYLIC ACID | 0.3 |
| | ADENOSINE | 0.1 |
| | PENTAERYTHRITYLTETRAETHYL-HEXANOATE | 0.5 |
| | *BUTYROSPERMUM PARKII* (SHEA) BUTTER | 2 |
| | BORON NITRIDE | 0.2 |
| First Mica | MICA coated with IRON OXIDES and with TITANIUM DIOXIDE | 0.3 |
| Second Mica | MICA coated with TITANIUM DIOXIDE and with IRON OXIDES | 0.5 |
| Second Pearlescent pigment | SYNTHETIC FLUORPHLOGOPITE coated with TITANIUM DIOXIDE and with TIN OXIDE | 0.65 |
| First Pearlescent uncoated pigment | SYNTHETIC FLUORPHLOGOPITE | 0.4 |
| | POLYMER | 2.1 |
| | PRESERVATIVE | 0.5 |
| | SILICON/OILS | 6.5 |
| | ORGANIC SOLVENT | 18.5 |
| | EMULSIFIERS | 2 |
| | WATER | Q.S. |

In making the formulations in the above table, the following procedure may be used. Organic solvent, preservatives, pH adjuster, disodium EDTA, caprylol salicylic acid and adenosine were introduced to the Main Kettle with the water and heat to 75 C. Once pH adjuster, disodium EDTA, caprylol salicylic acid and adenosine were completely solubilized, emulsifier was introduced, until it melted and homogenized until uniform. The Main Kettle was then cooled to room temperature and polymers were incorporated. Polymers were swept and homogenized until fully swelled. The oils and silicone were introduced. Once emulsion was homogeneous, the pearls and powders were incorporated with low homogenization. Last, more organic solvent was introduced while mixing and lightly homogenizing.

The ratio blend of pearlescent pigments and mica are described in Table 2.

TABLE 2

| | Ratio blend | | |
|---|---|---|---|
| Ingredients | Pearlescent Pigments or Mica | Ratio Blend | Color |
| SYNTHETIC FLUORPHLOGOPITE | First Pearlescent uncoated pigment | 0.2-0.3 | White |
| SYNTHETIC FLUORPHLOGOPITE coated with TITANIUM DIOXIDE and TIN OXIDE | Second Pearlescent pigment | 0.3-0.4 | White |
| MICA coated with TITANIUM DIOXIDE and yellow IRON OXIDES | Second Mica | 0.2-0.3 | Bronze |
| MICA coated with red IRON OXIDES (and) TITANIUM DIOXIDE | First mica | 0.1-0.2 | Pink |

The pearlescent uncoated and coated pigments have a white color when they stand on their own. The two different types of mica, depending of their coatings, have a different color on their own. The first mica of the blend from Table 2 is coated with one or more layers of red iron oxides. That first mica is then further coated with titanium dioxide. Thus, it displayed a pink color. The second mica of the blend from Table 2 is coated with one or more layers of titanium oxides. That second mica is then further coated with yellow iron oxides. Thus, it displayed a bronze color. The ratio blend described in Table 2 is the ratio in which each ingredient is present in the inventive composition. The unique ratio between each of the ingredients described in Table 2 result in a formula tone which is both appealing in bulk and flattering on Caucasian, Asian, Hispanic, African American and Indian skin tones.

Evaluation of Inventive Composition and Commercially Available Benchmark Products Table 3 below represents some of the characteristic of the particles of the inventive composition as well as commercially available benchmark products, from A through H. The characteristics have been evaluated by using a microscope analysis. From the microscope analysis, it is possible to characterize the particles morphology, their size and their density.

TABLE 3

Average size particles and particle density of Inventive Formula and commercially available benchmark products

| | Formula | | | | | | | | |
|---|---|---|---|---|---|---|---|---|---|
| | Inventive | A | B | C | D | E | F | G | H |
| Total area µm² | 238243 | 393931 | 41697 | 346362 | 507058 | 891615 | 317570 | 635504 | 734724 |
| Particle Density | 2467 | 3394 | 115 | 2562 | 3091 | 4736 | 1836 | 3207 | 6677 |
| Area ratio % | 10 | 17 | 2 | 15 | 21 | 38 | 13 | 27 | 31 |
| Total region area µm² | 2367624 | 2367624 | 2367624 | 2367624 | 2367624 | 2367624 | 2367624 | 2367624 | 2367624 |
| Average size µm² | 97 | 116 | 363 | 135 | 164 | 188 | 173 | 198 | 110 |
| Standard Deviation µm² | 99 | 109 | 297 | 144 | 215 | 207 | 192 | 239 | 91 |

Scale referring to Table 3:
Average Particle Size Scale:
  Below 100 um2=small average particle size
  Between 100 um2 and 200 um2=medium average particle size
  Above 200 um2=high average particle size
Particle Density Scale:
  Between 0 and 2500=small particle density
  Between 2500 and 5500=medium particle density
  Above 5500=high particle density The average size particles and the particle density of a composition are correlated to two of the characteristics of the products, the haze and the homogenizing power. The haze refers to the diffusivity of a product, and its ability to re-direct rays of light passing through as determined in a conventional drawdown test. The homogenizing power refers to the coverage of the skin compared to the Skin Color Chart.

The haze depends on the average size particle of the composition and the homogenizing power depends on the particle density. Depending on the diffusivity of the product and the coverage, the composition on the skin has a different response. It has been demonstrated that the higher the average size particle is the higher the haze. It has also been demonstrated that the higher the particle density is the higher the homogenizing power. Thus, when the particle size is between 110 and 198 um² (medium average particle size) such as the commercially available benchmark product represented in Table 3, the haze of the formula is high. One exception (Clinique B) was noticed. The average size particle for that formula is 363 um2, but the haze was not the highest. This was explained by the fact that even though the particles were large, the low particle density counter balanced the haze effect. But, it was also observed that with such large particle size and low particle density, the commercial product B presented a sheer and glittery coverage and the particle were visible. In the case of the inventive composition the particles are not visible. It is a positive effect for the consumers looking to have a healthy looking skin tone. The commercial product H was also an exception. The observed haze of this product was very high despite a small average particle size. In this case, the high haze effect was explained by the high particle density. Thus, in that case, the combination of a small particle size with a very high particle density exhibited a metallic and very pigmented coverage. In the case of the inventive composition, there are no metallic and pigmented coverage and responds to the demand of the consumers looking to have a healthy looking skin tone. In the case of the inventive example, the combination of the small average particle size with a medium particle density gave the product its uniqueness in terms of diffusivity and coverage. Indeed, the small average particle size (97 um2) gave the inventive composition a small haze effect and the medium particle density (2467) gave the inventive composition a good homogenizing power. Thus, the radiant and glowing effect works for any type of skin tone.

The invention claimed is:

1. A composition for topical application to the skin comprising:
   a. a first synthetic fluorphlogopite having an average particle size of 25 µm;
   b. a first mica having an average size of 42 µm or less, completely or partially coated with one or more layers of red iron oxides, further coated with titanium dioxide; and
   c. a second mica having an average size of 42 µm or less, completely or partially coated with one or more layers of titanium dioxide, further coated with iron dioxide.

2. The composition of claim 1, wherein the first synthetic fluorphlogopite is uncoated.

3. The composition of claim 1, further comprising a second synthetic fluorphlogopite having an average particle size of 25 µm or less, completely or partially coated with one or more layers of metal oxides.

4. The composition of claim 3, wherein the second synthetic fluorphlogopite is completely or partially coated with one or more layers of metal oxides chosen from the group consisting of titanium dioxide, tin dioxide, iron dioxide, aluminum dioxide, and mixtures thereof.

5. The composition of claim 4, wherein the second synthetic fluorphlogopite is completely or partially coated with titanium dioxide and tin dioxide.

6. The composition of claim 1, further comprising boron nitride.

7. The composition of claim 6, wherein the total amount of the boron nitride in the composition is from about 0.1% to about 7%, based on the total weight of the composition.

8. The composition of claim 1, wherein the composition is in the form of an emulsion, a powder, a cream-to-powder cosmetic, a gel, a pomade, a solution, a stick, or a suspension.

9. The composition of claim 1, wherein the composition is in the form of an oil-in-water emulsion.

10. The composition of claim 1, further comprising one or more skin active ingredients.

11. The composition of claim 10, wherein the one or more skin active ingredients are selected from the group consisting of a humectant, a moisturizing ingredient, an anti-aging agent, a depigmenting agent, an anti-wrinkle agent, an agent that treats oily skin, and a mixture thereof.

12. The composition of claim 11, wherein the one or more skin active ingredients are selected from the group consisting of adenosine, ascorbic acid, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, a coenzyme, and a mixture thereof.

13. A method of providing glow to skin comprising applying the composition of claim 1 to the skin.

* * * * *